(12) United States Patent
McLoughlin et al.

(10) Patent No.: US 10,500,341 B2
(45) Date of Patent: Dec. 10, 2019

(54) ASSEMBLY FOR AN AUTOINJECTOR DEVICE

(71) Applicants: Bespak Europe Limited, Hemel Hempstead (GB); UCB Biopharma SPRL, Brussels (BE)

(72) Inventors: Martin John McLoughlin, Oakington (GB); Ian Darnell, Oakington (GB); Matt Ekman, East Yorkshire (GB); Ian Anderson, Salford (GB); Neil Bentley Cammish, Salford (GB)

(73) Assignees: Bespak Europe Limited (GB); UCB Biopharma SPRL (BE)

( * ) Notice: Subject to any disclaimer, the term of this patent is extended or adjusted under 35 U.S.C. 154(b) by 338 days.

(21) Appl. No.: 14/909,689

(22) PCT Filed: Aug. 4, 2014

(86) PCT No.: PCT/GB2014/052387
§ 371 (c)(1),
(2) Date: Feb. 2, 2016

(87) PCT Pub. No.: WO2015/015230
PCT Pub. Date: Feb. 5, 2015

(65) Prior Publication Data
US 2016/0175531 A1    Jun. 23, 2016

(30) Foreign Application Priority Data

Aug. 2, 2013 (GB) .................................. 1313888.8

(51) Int. Cl.
*A61M 5/31* (2006.01)
*A61M 5/24* (2006.01)
*A61M 5/20* (2006.01)

(52) U.S. Cl.
CPC ............ *A61M 5/3134* (2013.01); *A61M 5/20* (2013.01); *A61M 5/2033* (2013.01); *A61M 5/24* (2013.01);
(Continued)

(58) Field of Classification Search
CPC .............. A61M 5/3134; A61M 5/2033; A61M 2005/3142; A61M 5/24; A61M 2005/2073; A61M 5/50; A61M 5/5086; A61M 5/508
See application file for complete search history.

(56) References Cited

U.S. PATENT DOCUMENTS 4,985,000 A    1/1991  Tengler et al.
6,223,733 B1   5/2001  Busato et al.
(Continued)

FOREIGN PATENT DOCUMENTS

CN    102917737 A    2/2013
CN    103533975 A    1/2014
(Continued)

OTHER PUBLICATIONS

International Preliminary Report on Patentability dated Feb. 11, 2016 in International Patent Appl. No. PCT/GB2014/052387.
(Continued)

*Primary Examiner* — Nathan R Price
*Assistant Examiner* — Tasnim Mehjabin Ahmed
(74) *Attorney, Agent, or Firm* — Lerner, David, Littenberg, Krumholz & Mentlik, LLP

(57) ABSTRACT

An assembly for an auto injector device, the assembly including a syringe support for supporting a syringe by limiting forward axial movement of the syringe relative to the syringe support, and a guard element attachable to the syringe support by an attachment so that the guard element is axially restrained both axially forwardly and axially (Continued)

rearwardly relative to the syringe support by the attachment. Forwardly directed axial loads received by the guard element are transmitted to the syringe support via the attachment.

33 Claims, 4 Drawing Sheets

(52) U.S. Cl.
CPC . *A61M 2005/3142* (2013.01); *A61M 2205/19* (2013.01)

(56) References Cited

U.S. PATENT DOCUMENTS

| | | | |
|---|---|---|---|
| 6,305,908 | B1 | 10/2001 | Hermann et al. |
| D660,958 | S | 5/2012 | McLoughlin et al. |
| 2001/0001822 | A1 | 5/2001 | Chambers et al. |
| 2002/0012764 | A1 | 1/2002 | Magee et al. |
| 2003/0050592 | A1 | 3/2003 | Slate et al. |
| 2004/0035491 | A1 | 2/2004 | Castellano |
| 2005/0131355 | A1 | 6/2005 | Kirchhofer et al. |
| 2006/0184117 | A1 | 8/2006 | Knight et al. |
| 2007/0068531 | A1* | 3/2007 | Matlock ............ A61M 16/0465 128/207.15 |
| 2008/0082044 | A1* | 4/2008 | Sharon ................... A61M 5/24 604/89 |
| 2008/0195056 | A1 | 8/2008 | Bishop et al. |
| 2008/0317605 | A1 | 12/2008 | Amley et al. |
| 2009/0209883 | A1 | 8/2009 | Higgins et al. |
| 2010/0016795 | A1 | 1/2010 | McLoughlin |
| 2010/0185148 | A1 | 7/2010 | Gillespie, III et al. |
| 2012/0016795 | A1 | 1/2012 | Hill et al. |
| 2012/0289905 | A1 | 11/2012 | Julian et al. |
| 2013/0112521 | A1 | 5/2013 | Ekman et al. |
| 2013/0123710 | A1 | 5/2013 | Ekman et al. |
| 2013/0138048 | A1 | 5/2013 | Kemp et al. |
| 2013/0138049 | A1 | 5/2013 | Kemp et al. |
| 2013/0144220 | A1 | 6/2013 | Cleathero et al. |
| 2013/0150801 | A1 | 6/2013 | Ekman et al. |
| 2013/0190694 | A1 | 7/2013 | Barrow-Williams et al. |
| 2013/0338593 | A1 | 12/2013 | Wozencroft |
| 2014/0148763 | A1 | 5/2014 | Karlsson et al. |
| 2014/0148784 | A1 | 5/2014 | Anderson et al. |
| 2014/0228769 | A1 | 8/2014 | Karlsson et al. |
| 2014/0257191 | A1 | 9/2014 | Cowe |
| 2014/0309591 | A1 | 10/2014 | Holmqvist |
| 2014/0330215 | A1 | 11/2014 | Kikuchi et al. |
| 2015/0224262 | A1 | 8/2015 | Jugl et al. |
| 2017/0312173 | A1 | 11/2017 | Klintenstedt et al. |

FOREIGN PATENT DOCUMENTS

| | | |
|---|---|---|
| CN | 103619378 A | 3/2014 |
| EP | 1681070 A1 | 7/2006 |
| EP | 1952835 A1 | 8/2008 |
| GB | 2445090 A | 6/2008 |
| GB | 2463071 A | 3/2010 |
| GB | 2466371 A | 6/2010 |
| GB | 2475917 A | 6/2011 |
| JP | 3052991 U | 10/1998 |
| JP | 2002518107 A | 6/2002 |
| JP | 2012082262 A | 4/2012 |
| JP | 2013522481 A | 6/2013 |
| JP | 2014506493 A | 3/2014 |
| WO | 9855168 A1 | 12/1998 |
| WO | 9965547 A1 | 12/1999 |
| WO | 02076374 A1 | 10/2002 |
| WO | 2005070481 A1 | 8/2005 |
| WO | 2007083115 A1 | 7/2007 |
| WO | 2011070346 A1 | 6/2011 |
| WO | 2011112309 A1 | 9/2011 |
| WO | 2012103141 A1 | 8/2012 |
| WO | 2012145685 A1 | 10/2012 |
| WO | 2013077800 A1 | 5/2013 |
| WO | 20140033141 A1 | 3/2014 |

OTHER PUBLICATIONS

International Search Report and Written Opinion for Application No. PCT/GB2014/052387 dated Apr. 23, 2015.
Minnesota Rubber and Plastics, Titled "Elastomers and Thermoplastics Engineering Design Guide", 4 pages.
Minnesota Rubber and Plastics; Titles "Elastomers and Thermoplastics Engineering Design Guide Rubber over-Molding", https://www.mnrubber.com/Design_Guide/2-13.html, 5 pgs, Downloaded Jul. 17, 2019, Copyright 2019.
W. Narhi, E. Evans; Rubber World, 2008, Titled: "TPV overmolding", 4 pages.

* cited by examiner

ASSEMBLY FOR AN AUTOINJECTOR DEVICE

CROSS-REFERENCE APPLICATIONS

The present application is a national phase entry under 35 U.S.C. § 371 of International Application No. PCT/GB2014/052387 filed Aug. 4, 2014, published in English, which claims priority from GB 1313888.8 filed Aug. 2, 2013, all of which are incorporated herein by reference.

This invention relates to an assembly for an autoinjector device, and in particular, to an assembly for an autoinjector device that reduces the risk of syringe damage during use of the autoinjector device.

BACKGROUND

Typically, pre-filled syringes supplied by pharmaceutical companies are made from glass or similarly hard but brittle materials. Many such pre-filled syringes are manufactured to a recognized industry "standard" and are used in autoinjector devices for delivery of the pre-filled medicament. An example of an autoinjector device employing such a standard pre-filled syringe is described in WO-A-2007/083115 (The Medical House plc) where, within the device, a drive element acts on the flange of the syringe to advance it axially forwardly to insert the needle of the syringe into an injection site.

WO-A-2011/070346 (The Medical House Ltd) describes a syringe flange protector in the form of a spacer element that seeks to reduce the drive load applied to the syringe flange by redirecting it radially inwardly towards the main barrel of the syringe.

There remains a need to further minimize the risk of syringe breakage in autoinjector devices, since any breakage may lead to jamming of the device and, ultimately, failure to deliver the dose of medicament with potentially fatal consequences.

The present invention therefore seeks to minimize the risk of syringe breakage in autoinjector devices.

BRIEF SUMMARY OF THE DISCLOSURE

In accordance with a first aspect of the present invention there is provided an assembly for an autoinjector device, the assembly including:
  a syringe support for supporting a syringe by limiting forward axial movement of the syringe relative to the syringe support; and
  a guard element attachable to the syringe support;
  wherein the guard element is attachable to the syringe support so that the guard element is axially restrained both axially forwardly and axially rearwardly relative to the syringe support, wherein attachment of the guard element to the syringe support is by abutment of first abutment features on the syringe support and second abutment features on the guard element;
  wherein forward axial movement of the guard element relative to the syringe support is limited by the abutment of the first and second abutment features;
  and wherein forwardly directed axial loads received by an axially rearward surface of the guard element are transmitted to the syringe support via the abutment of the first and second abutment features.

Thus, the guard element is attachable to the syringe support such that, when attached, relative axial movement between the guard element and the syringe support is limited by abutment of the first and second abutment features. That is, abutment of the first and second abutment features limits relative axial movement and is responsible for transferring load applied to the guard element to the syringe support. A syringe that may be installed in the syringe support (prior to attachment of the guard element) will not experience any loading that is applied to the rear of the guard element, since the guard element acts as a loading "bridge" that transmits load from a driving member to the syringe support without applying axial loading to the syringe. In certain embodiments, the guard element is attachable to a rear end of the syringe support.

Said second abutment features of said guard element may include a plurality of axially forwardly extending legs, and said first abutment features of said syringe support may include an external flange, and forward axial movement of the guard element relative to the syringe support may be limited by abutment of said plurality of axially forwardly extending legs against said external flange. Said plurality of axially forwardly extending legs may form part of at least a pair of clasps, where each clasp includes a pair of said axially forwardly extending legs and a front cross beam extending circumferentially to connect the two legs of each pair of axially forwardly extending legs. Each of said front cross beams may form the axially forwardmost portion of each respective clasp.

An axially forwardly facing surface of each front cross beam may be tapered, the axially forwardly facing surface extending axially rearwardly in a radially outward direction, and an axially rearwardly facing surface of said external flange is also tapered in at least parts, the axially rearwardly facing surface of said parts extending axially rearwardly in a radially outward direction so as to be complementary to the axially forwardly facing surface of each front cross beam.

The syringe support may include third abutment features and the guard element may include fourth abutment features and rearward axial movement of the guard element relative to the syringe support is limited by the abutment of the third and fourth abutment features.

Said third abutment features of said syringe support may include outwardly radially extending elbows and said fourth abutment features of said guard element include said front cross beams and rearward axial movement of the guard element relative to the syringe support is limited by the abutment of the elbows against said front cross beams. Axially rearwardly extending legs may extend from said elbows.

Said front cross beams may have a recessed portion for facilitating assembly of the front cross beams over the axially rearwardly extending legs of said syringe support.

Said clasps may each include a second cross beam that extends circumferentially to connect the two legs of each pair of axially forwardly extending legs, each second cross beam being axially rearward and axially spaced from the respective front cross beam.

The syringe support may include hooks that are configured to latch onto the guard element and limit rearward axial movement of the guard element relative to the syringe support. Each of said hooks may be disposed on an axially rearwardly extending leg of said syringe support.

The legs of each of said pair of axially forwardly extending legs of each clasp may be circumferentially spaced to receive one of said axially rearwardly extending legs of said syringe support. Said front cross beams may have a recessed portion for facilitating assembly of the front cross beams over the axially rearwardly extending legs of said syringe support.

The guard element defines an axially rearward surface for receiving an axial drive (for causing movement of the syringe support, for example). In certain embodiments, the axially rearward surface for receiving axial drive is an axially rearward surface of a flange.

Said guard element may define a central bore extending in an axial direction and the flange may extend radially outwardly from the bore. The axially rearward facing surface of the flange may slope axially forwardly along radial directions away from said bore. Said axially rearward facing surface of said flange may correspond to part of the surface of a conic frustum.

Said guard element may further comprise locating features for co-axially aligning the guard element with the rear end of a syringe. Said locating features may comprise an axially forwardly extending spigot extending from the axially forwardly facing surface of the flange, the spigot defining part of said bore.

The guard element may be assembled on said syringe support. The assembly may further comprise a syringe supported by said syringe support, wherein at least part of said guard element is axially rearward of at least part of said syringe. Said syringe may comprise a barrel having an outlet at a forward end, a needle fluidly connected to said outlet, an open rear end, a plunger element moveable within said barrel, a plunger rod connected to said plunger element for moving said plunger element within said barrel, and a rear syringe flange extending radially outwardly from a rear end of the barrel.

An axially forwardly facing side of the guard element may be shaped so as to be complementary to the profile of the rear syringe flange.

The spigot may be shaped so as to be complementary to the profile of the open rear end of the barrel.

Axially rearward movement of the syringe received in the syringe support may be constrained by the guard element. In certain embodiments, some limited axial movement of the syringe in the syringe support may be permitted. In other embodiments, substantially no axial movement of the syringe in the syringe support is permitted due to the presence of the guard element.

The syringe may contain a liquid drug formulation, and, in particular embodiments, the barrel of said syringe has a volume corresponding to a single dose of said liquid drug formulation. Said liquid drug formulation may be arranged for rest at from 2-8° C. and for injected delivery at from 18-30° C. The liquid drug formulation may have a viscosity of less than 120 mPa·s at a delivery temperature of 20° C. The liquid drug formulation may comprise an aqueous formulation of a therapeutic biologic type drug. Said biologic type drug may comprise an immunoglobulin or a fragment thereof. Said biologic type drug may comprise a PEGylated or mPEGylated antibody fragment. Said aqueous formulation may comprise additional formulation component selected from the group consisting of buffers, NaCl, and pH modifiers. The concentration of the drug in the liquid drug formulation may be greater than 100 mg/ml.

In accordance with a second aspect of the present invention, there is provided an autoinjector device including the assembly as described above.

In accordance with an example, there is provided a guard element for use with a syringe and configured to be positioned at least partly rearwardly of a flange of the syringe, the guard element defining a central bore extending in an axial direction and having a flange around the bore extending radially outwardly, where the flange has an axially forwardly facing surface and an axially rearward facing surface, and the axially rearward facing surface slopes axially forwardly along radial directions away from said bore and is configured for receiving axial drive.

The guard element may further comprise locating features for locating the guard element on the rear end of a syringe. Said locating features may comprise an axially forwardly extending spigot extending from the axially forwardly facing surface of the flange, the spigot defining part of said bore. Said axially rearward facing surface of said flange may correspond to part of the surface of a conic frustum. The guard element may further comprise a plurality of axially forwardly extending legs. Said plurality of axially forwardly extending legs may form part of at least a pair of clasps, where each clasp includes a pair of said axially forwardly extending legs and a front cross beam extending circumferentially to connect the two legs of each pair of axially forwardly extending legs. Each of said front cross beams may form the axially forwardmost portion of each respective clasp. An axially forwardly facing surface of each front cross beam may be tapered, the axially forwardly facing surface extending axially rearwardly in a radially outward direction. Said front cross beams may have a recessed portion for facilitating assembly of said guard assembly on a syringe support. Said clasps may each include a second cross beam that extends circumferentially to connect the two legs of each pair of axially forwardly extending legs and is axially rearward and axially spaced from said front cross beam.

In accordance with an example, there is provided an assembly including a guard element as described above, and a syringe. Said syringe may comprise a barrel having an outlet at a forward end, a needle fluidly connected to said outlet, an open rear end, a plunger element moveable within said barrel, a plunger rod connected to said plunger element for moving said plunger element within said barrel, and a rear syringe flange extending radially outwardly from a rear end of the barrel.

An axially forwardly facing side of the guard element may be shaped so as to be complementary to the profile of the rear syringe flange.

The spigot may be shaped so as to be complementary to the profile of the open rear end of the barrel.

The syringe may contain a liquid drug formulation, and, in particular embodiments, the barrel of said syringe has a volume corresponding to a single dose of said liquid drug formulation. Said liquid drug formulation may be arranged for rest at from 2-8° C. and for injected delivery at from 18-30° C. The liquid drug formulation may have a viscosity of less than 120 mPa·s at a delivery temperature of 20° C. The liquid drug formulation may comprise an aqueous formulation of a therapeutic biologic type drug. Said biologic type drug may comprise an immunoglobulin or a fragment thereof. Said biologic type drug may comprise a PEGylated or mPEGylated antibody fragment. Said aqueous formulation may comprise additional formulation component selected from the group consisting of buffers, NaCl, and pH modifiers. The concentration of the drug in the liquid drug formulation may be greater than 100 mg/ml.

In accordance with an example, there is provided an autoinjector device including the assembly described above.

In accordance with an example, there is provided a syringe support for supporting a syringe by limiting forward axial movement of the syringe relative to the syringe support, the syringe support having an external flange and hooks, each hook being disposed on an axially rearwardly extending leg of said syringe support.

In accordance with an example, there is provided a syringe support for supporting a syringe by limiting forward axial movement of the syringe relative to the syringe support, the syringe support having an external flange and outwardly radially extending elbows axially rearward of the external flange.

The above-described syringe support may further comprise at least one radially inward projection for supporting a syringe thereon.

BRIEF DESCRIPTION OF THE DRAWINGS

Embodiments of the invention are further described hereinafter with reference to the accompanying drawings, in which.

DETAILED DESCRIPTION

Figure 1A:
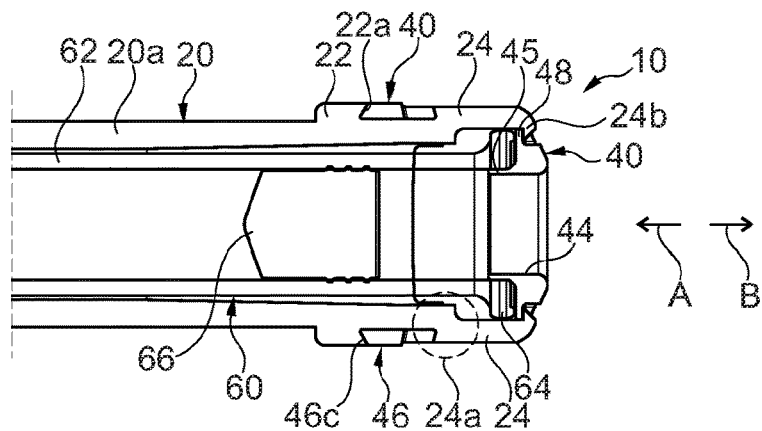
FIG. 1A is a cross-sectional view of an assembly according to an embodiment of the present invention with a syringe installed, FIGS. 1B and 1C each show a side view of the assembly of FIG. 1A where assembly of FIG. 1C is rotated 90° relative to the assembly of FIG. 1B.
Figure 1B:
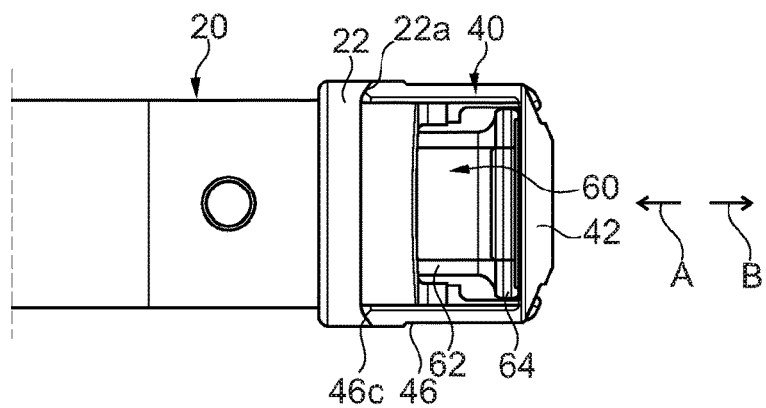
Figure 1C:
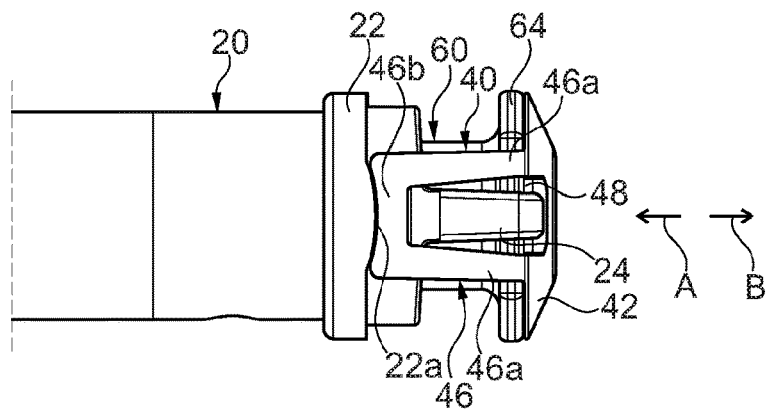

FIG. 1A is a cross-sectional view of an assembly 10 according to an embodiment of the present invention. FIGS. 1B and 1C each show a side view of the assembly of FIG. 1A where the assembly of FIG. 1C is rotated 90° relative to the assembly of FIG. 1B. The assembly 10 includes a syringe support 20 and a guard element 40. In the arrangement shown in FIG. 1A, a syringe 60 is installed within the assembly 10. The syringe support 20 supports the syringe 60 so that axial movement of the syringe support 20 results in axial movement of the syringe 60 therein such as during forward axial movement of the syringe support 20 and syringe 60 from a pre-use position to an injection position within an autoinjector device. The syringe support 20 may therefore be considered to be a syringe carrier. The arrows labeled A and B in the Figures indicate the "axial" directions where A represents the forward axial direction (i.e. towards the injection site) and B represents the rearward axial direction (i.e. away from the injection site). Other directions and orientations referred to throughout this application (for example, radial and circumferential) are relative to the axial directions A, B. The directions A and B may be considered to be parallel to a "longitudinal direction" of the assembly of the present invention, or indeed any larger device incorporating the assembly, or any components of the assembly.

In preferable embodiments, the syringe support 20 supports the syringe 60 at a forward end of the syringe 60, for example on an internal flange of the syringe support 20. In particularly preferable embodiments, the syringe support 20 includes some or all of the features of the syringe support means described in WO-A-2007/083115. However, in alternative embodiments within the scope of the present invention, the syringe 60 may be supported by the syringe support 20 at points of the syringe 60 other than its forward end.

The syringe 60 may be a standard prefilled syringe and includes a barrel 62 having a rear syringe flange 64 and a stopper 66 disposed within the barrel and moveable therein. Typically, in use, the stopper 66 is moved by a plunger rod (not shown) or similar element, to pressurize fluid contained in the barrel 62 and expel it from an open front end of the syringe 60. The syringe 60 may include a needle (not shown) at its forward end for penetrating an injection site and facilitating the expulsion of fluid form the barrel 62.

The guard element 40 is a separate component relative to the syringe support 20 and is attachable to a rear end of the syringe support 20. The attachability of the guard element 40 permits the syringe 60 to be inserted into the syringe support 20 prior to the attachment of the guard element 40. An integral guard element 40 and syringe support 60 would not permit the insertion of the syringe 60 without sacrificing features that give rise to the benefits associated with the present invention.

As shown in FIGS. 1A to 1C, the syringe support 20 is generally tubular and has an external flange 22 towards its rear end that acts as an abutment element which the guard element 40 abuts against to prevent further forward axial movement of the guard element 40 relative to the syringe support 20. The external flange 22 has a rearwardly facing undercut section 22a for engaging with the guard element 40 and minimizing the risk of inadvertent movement of the guard element 40 relative to the syringe support 20.

A main body 20a of the syringe support 20 has an internal diameter that is larger than the external diameter of the syringe barrel 62 such that the syringe 60 may be inserted into the syringe support 20 during assembly. In preferable embodiments, the annular space between the main body 20a of the syringe support 20 and the syringe barrel 62 (when installed) is small so as to minimize radial movement of the syringe 60 within the syringe support 20 thereby reducing the risk of syringe 60 breakage. The internal diameter of the main body 20a of the syringe support 20 is smaller than the outer diameter of the rear syringe flange 64 of the syringe 60 so that the rear syringe flange 64 cannot pass into the main body 20a. In preferable embodiments, the syringe 60 is supported in the syringe support 20 (e.g. by an abutment) such that forward axial movement of the syringe 60 is limited relative to the syringe support 20 to a degree where it would not be possible for the rear syringe flange 64 to enter the main body 20a in any event. Similarly, axially rearward movement of the syringe within the syringe support is constrained by the guard element.

The external flange 22 of the syringe support 20 is located close to the rear end of the main body 20a, however it is not at the actual rear end but axially spaced therefrom.

The syringe support 20 has a pair of rearwardly axially extending legs 24 extending from the rear end of the main body 20a axially rearward of the external flange 22. Each of the pair of legs 24 is diametrically opposite the other of the pair and each extends from the main body 20a via an elbow 24a that extends radially outwardly. Due to the elbows 24a, the internal diameter of the legs 24 (when considered as a pair) is greater than the internal diameter of the main body 20a. The internal diameter of the legs 24 is preferably similar to the outer diameter of the rear syringe flange 64 of the syringe 60 such that the rear flange 60 may be accommodated between the legs 24 but there is minimal space between the legs 24 and the rear syringe flange 64. Additionally, in the non-limiting preferable embodiment shown in FIGS. 1A to 1C, the outer diameter of the legs 24 (when considered as a pair) is substantially the same as the outer diameter of the external flange 22. The legs 24 each have a hook 24b that extends both radially inwardly and axially forwardly so as to be capable of engaging with the guard element 40 and preventing rearward axial movement of the guard element 40 relative to the syringe support 20 (as described in more detail below). In the embodiment shown in FIGS. 1A to 1C, the hooks 24b are disposed at the extreme rear end of the legs 24, although in alternative embodiments, this need not necessarily be the case.

In the preferable embodiment shown in the Figures, the guard element 40 has a conical or otherwise sloped rear surface 42 around a central bore 44. In particular, the rear surface 42 of the guard element slopes axially forwardly along an outwardly radial direction from the edge of the bore 44. The guard element 40 has an axially forwardly extending spigot 45 that is centrally located and has an outer diameter suitable for locating in and forming a close fit with the inside of the barrel 62 of the syringe 60. An axially forwardly facing side of the guard element 40 is shaped so as to be complementary to the profile of the syringe flange 64. Similarly, the spigot 45 is shaped so as to be complementary to the profile of the barrel 62 in which it fits. Such complementary features improve the fit of the guard element 40 against the syringe 60. The spigot 45 forms a step on the axially forwardly facing side of the guard element 40 so that a surface of the guard element 40 extends radially beyond the bore 44 and prevents the entire guard element 40 from entering the inside of the barrel 62.

The guard element 40 extends radially beyond the rear syringe flange 64 and has an axially forwardly extending clasp 46 that is positioned radially outward of the rear syringe flange 64 when the spigot 45 is located in the bore 44, as shown in the Figures. The clasp 46 includes a pair of circumferentially spaced legs 46a that extend axially forwardly, and a cross beam 46b that extends circumferentially between the two legs 46a, linking them together. The forwardmost surface of the clasp 46c is beveled so as to be complementary to the rearwardly facing undercut section 22a of the external flange 22 and be configured to engage therewith with reduced risk of inadvertent axial or radial relative movement therebetween. This arrangement provides an abutment that limits forward axial movement of the guard element 40 relative to the syringe support 20 and permits axial load to be transmitted from the guard element 40 to the syringe support 20. Whilst this is a preferable embodiment, less preferable embodiments may feature non-tapered (i.e. no axial variation along a radial direction) interface surfaces between the clasp 46 and the external flange 22. These arrangements would still achieve the desired abutment for limiting forward axial movement of the guard element 40 relative to the syringe support 20 but would be less effective at minimizing the risk of the clasp 46 inadvertently flexing radially outwardly and sliding axially forwardly over the external flange 22.

In the preferable embodiment shown in the Figures, the circumferential space between the two legs 46a of the clasp 46 accommodates the rearwardly axially extending legs 24 of the syringe support 20. Additionally, the guard element 40 has a pair of axially rearwardly facing receiving surfaces 48 for receiving the hooks 24b of the legs of the syringe support 20 where each of the axially rearwardly facing receiving surfaces tapers axially rearwardly in a radially outwardly direction so as to be complementary to the forward facing surface of each hook 24b. When engaged on the axially rearwardly facing receiving surfaces 48, the hooks 24b limit rearward axial movement of the guard element 40 relative to the syringe support 20. The combination of the abutment between the clasp 46 and the external flange 22 and the engagement of the hooks 24b on the axially rearwardly facing receiving surfaces 48 results in the guard element 40 being limited in both the forward and rearward axial directions relative to the syringe support 20 and therefore being axially "captured" relative thereto. Some small relative axial movement may be possible due to manufacturing tolerances, however it is preferable for any axial movement to be as small as possible.

The guard element 40 forms a loading bridge that transmits axial force received from the rear of the guard element axially forwardly into the syringe support 20 via the external flange 22. The assembly is configured so that no axial load is transmitted from the guard element 40 to the syringe 60, and the syringe is therefore protected from potentially damaging forces during use. One factor that contributes to the syringe avoiding applied axial loading is the relationship between the supporting of the syringe by the syringe support 20 and the respective axial lengths of the clasps 46 and the axially rearwardly extending legs 24 of the syringe support 20. To avoid loading, the syringe 60 should be "floating" within the assembly 10 of the syringe support 20 and the guard element 40. That is, some limited axial movement of syringe in the syringe support may be permitted.

Figure 2A:
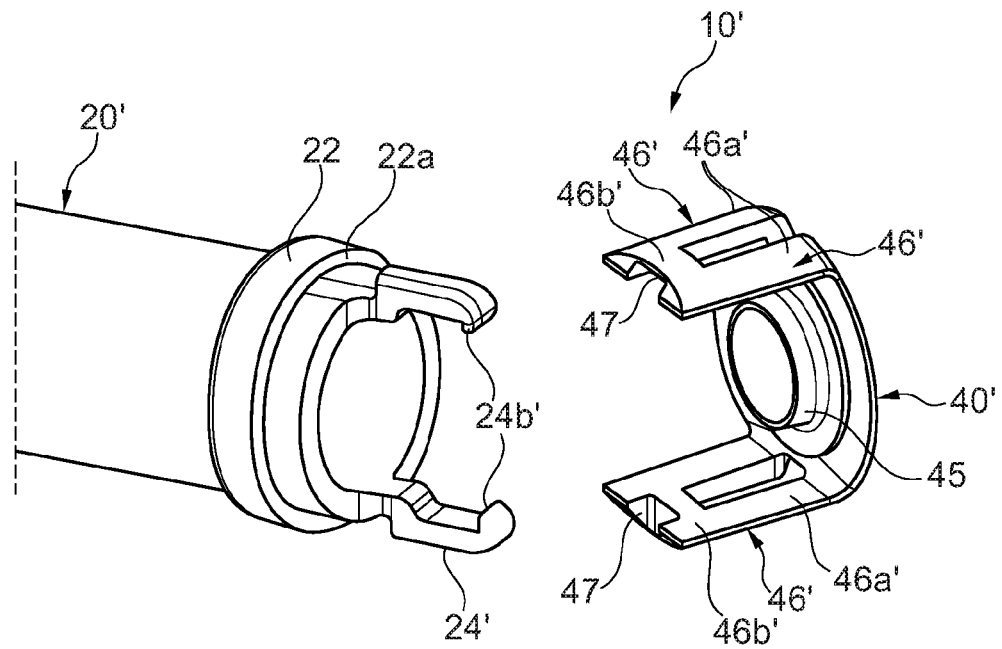
FIG. 2A shows an unassembled assembly in accordance with an alternative embodiment of the present invention.
Figure 2B:
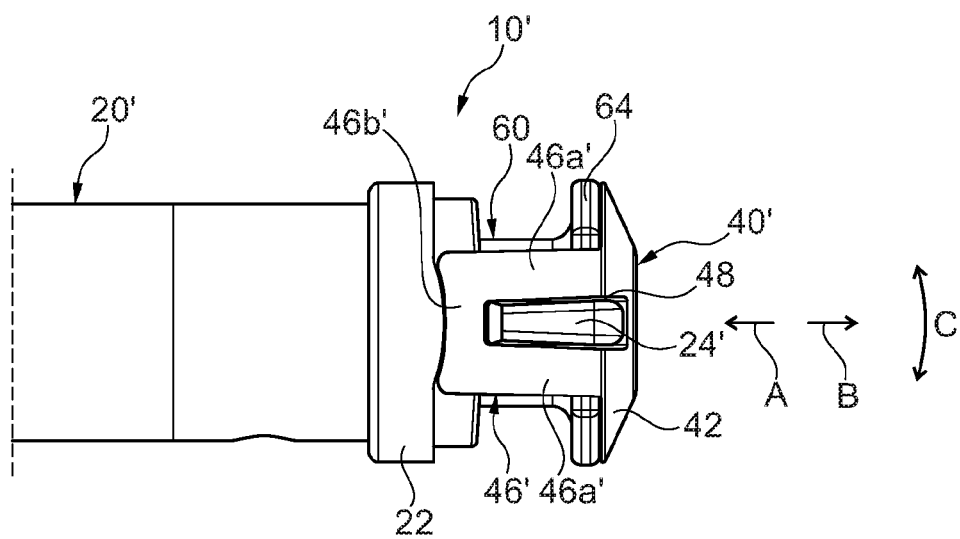
FIG. 2B shows a side view of the assembly of FIG. 2A assembled with a syringe installed.

FIGS. 2A and 2B show a modified assembly 10' in accordance with an alternative embodiment of the present invention. The modified assembly 10' includes a modified guard element 40' and a modified syringe support 20'. The modified guard element 40' and syringe support 20' are each largely the same as the guard element 40 and syringe support 20 described above in relation to FIGS. 1A to 1C, however modified components are indicated with a prime/dash (') and new components/features are indicated by a new numeral. For example, the modified guard element 40' of FIGS. 2A and 2B has a modified clasp 46' that differs in two respects in comparison with the clasp 46 of FIGS. 1A to 1C. The modified clasp 46' still includes two pairs of circumferentially spaced legs 46a' that extend axially forwardly, and a cross beam 46b' that extends circumferentially between the two legs 46a' of each pair, linking the respective pair together. However, each cross beam 46b' includes a recessed portion 47 on its radially inward side. Each recessed portion 47 is tapered so as to facilitate assembly of guard element 40' onto the syringe support 20' by assisting the clasps 46' over the modified axially rearwardly extending legs 24' of the modified syringe support 20'.

Secondly, the legs 46a' of the clasp 46' are wider in a circumferential direction in comparison with the legs 46a of the guard element 40 of FIGS. 1A to 1C. This widening is possible since the axially rearwardly extending legs 24' of the modified syringe support 20' are narrower in a circumferential direction in comparison with the legs 24 of FIGS. 1A to 1C. The wider legs 46a' of the clasp 46' improve cross-sectional area strength and reduce the risk of the guard element 40' breaking or deforming under load.

Additionally, the axially rearwardly extending legs 24' are tapered in an axial direction, with the legs 24' increasingly widening in a circumferential direction along the axial rearward direction. The axially rearwardly extending legs 24' form a close fit with the clasp 46' and reduce "rocking" of the guard element 40' relative to the syringe support 20' along directions indicated by double arrow C in FIG. 2B. Rocking may alternatively be mitigated where the clasp 46' does not necessarily form a close fit entirely around the legs 24' by lugs located on either of the legs 24' or the clasp 46' for at least forming a close fit at selected locations and minimized relative movement.

Figure 3A:
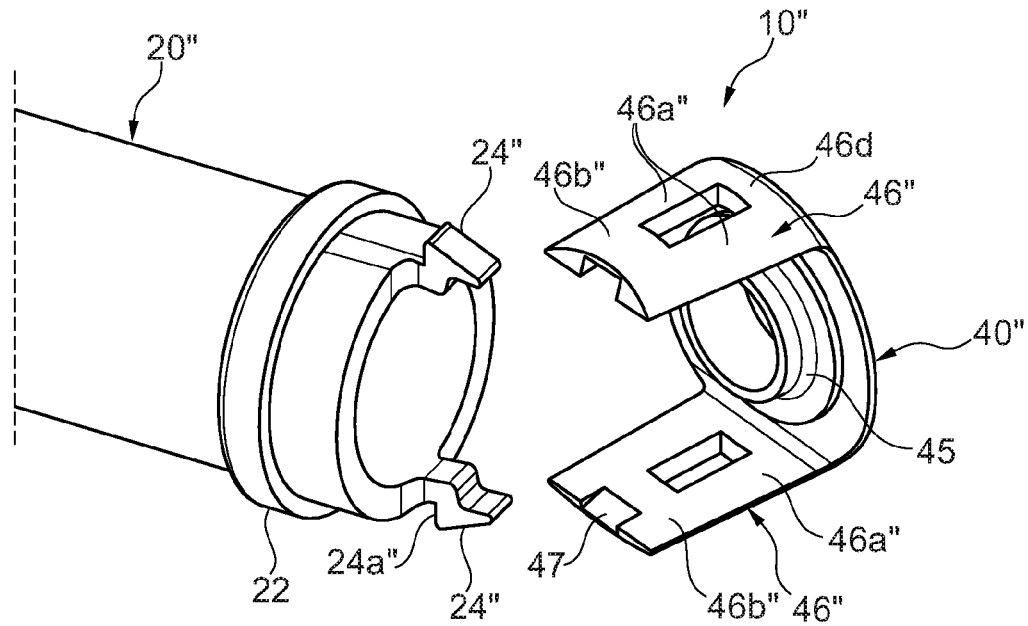
FIG. 3A shows an unassembled assembly in accordance with a further alternative embodiment of the present invention.
Figure 3B:
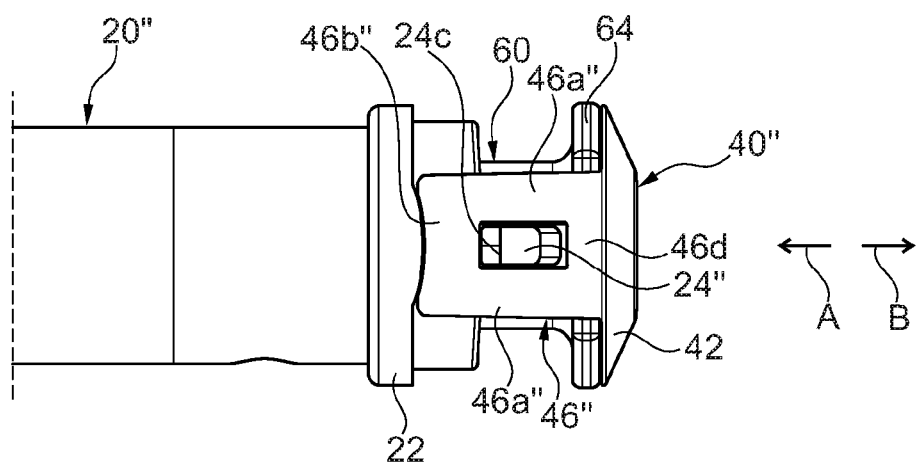
FIG. 3B shows a side view of the assembly of FIG. 3A assembled with a syringe installed.

FIGS. 3A and 3B show an alternative embodiment of an assembly 10" in accordance with the present invention. The modified assembly 10" includes a modified guard element 40" and a modified syringe support 20". The modified guard element 40" and syringe support 20" are each largely the same as the guard element 40 and syringe support 20 described above in relation to FIGS. 1A to 1C, however modified components are indicated with a double prime/dash (") and new components/features are indicated by a new numeral. The modified clasp 46" still includes two pairs of circumferentially spaced legs 46a" that extend axially forwardly, and a cross beam 46b" that extends circumferentially between the two legs 46a" of each pair, linking the respective pair together. Additionally, the clasp 46" has a rear cross beam 46d axially rearward and axially spaced from the cross beam 46b", where the rear cross beam 46d extends circumferentially between the legs 46a". The pair of cross-beams 46d, 46b" and the pair of legs 46a" define an aperture for receiving the axially rearwardly extending legs 24".

As shown in FIGS. 3A and 3B, the axially rearwardly extending legs 24" of the modified syringe support 20" are axially shorter than the legs 24,24' of FIGS. 1A-1C and FIGS. 2A-2B. The legs 24" do not have radially inwardly extending hooks (c.f. hooks 24b,24b') and do not latch onto rearwardly facing receiving surfaces (c.f. rearwardly facing receiving surfaces 48). Instead, the elbow 24a" of the legs 24" abut against the cross beam 46b" to limit rearward axial movement of the guard element 40" relative to the syringe support 20". In the assembled configuration, as shown in FIG. 3B, there is an axial gap between the axially forwardly facing side of the elbow 24a" and the axially rearwardly facing side of the cross beam 46b". This gap determines the degree of possible relative axial movement between the guard element 40" and the syringe support 20". In preferable embodiments, the elbow 24a" may be tapered, extending axially forwardly in a radially outward direction, to engage with a complementary rearwardly facing surface of the cross beam 46b". In this preferable arrangement, the clasp 46" engages more firmly with the syringe support 20" when moved axially rearwardly relative thereto, as the risk of the clasp 46" deforming so as to slide over the legs 24" is reduced.

The rearwardly axially extending legs 24,24' of the embodiments described above in relation to FIGS. 1A to 1C and 2A to 2B may also include an elbow, where the cross beam 46b,46b' abuts the elbow to limit rearward axial movement of the guard element 40,40' in the unlikely event that the hooks 24b,24b' fail.

The guard element 40" of FIGS. 3A and 3B is shown with the recessed portion 47 present on each clasp 46". Whilst it is preferable for this feature to be present and assist assembly of the guard element 40" onto the syringe support 20", embodiments within the scope of the present invention may not have this feature, but retain the other described features of the embodiment of FIGS. 3A and 3B. Indeed, the recessed portion 47 may or may not be present on the clasps 46,46', 46" within the scope of the present invention.

Similarly, whilst the rear surface 42 of the guard elements 40,40',40" is described above as being conical or otherwise sloped, in alternative embodiments within the scope of the present invention, the rear surface 42 may not be sloped (i.e. not varying axially along a radial direction). Such embodiments may still include any of the described features of the embodiments of FIGS. 1A-1C, 2A-2B and 3A-3C. It is noted, however, that a conical or otherwise sloped rear surface 42 is preferable in that it facilitates a driving member to cease contact with the guard element 40,40',40" once the driving member has acted thereon to move the syringe support 20,20',20" (and hence syringe 60 contained therein) to a position suitable for delivery (i.e. when a needle of the syringe 60 has penetrated an injection site to a sufficient depth). For example, a conical or otherwise sloped rear surface 42 is particularly suitable for use in autoinjectors having driving elements that have flexible legs or tags that initially engage with the guard element 40,40',40" to apply a load to the syringe support 20,20',20" to move the syringe 60, and then flex radially outwardly into an aperture of a housing of the autoinjector when a specific axial position is reached. The conical or otherwise sloped surface 42 will reduce the risk of the flexible legs or tags failing to flex into the aperture and thus disengaging with the guard element 40,40',40" which may cause the device to jam and the dose of medicament to not be delivered. Guard elements 40,40', 40" having a conical or otherwise sloped rear surface 42 are particularly suited for use in devices where the drive element is equivalent to the inner housing component described in the publication WO-A-2005/070481.

Figure 4:
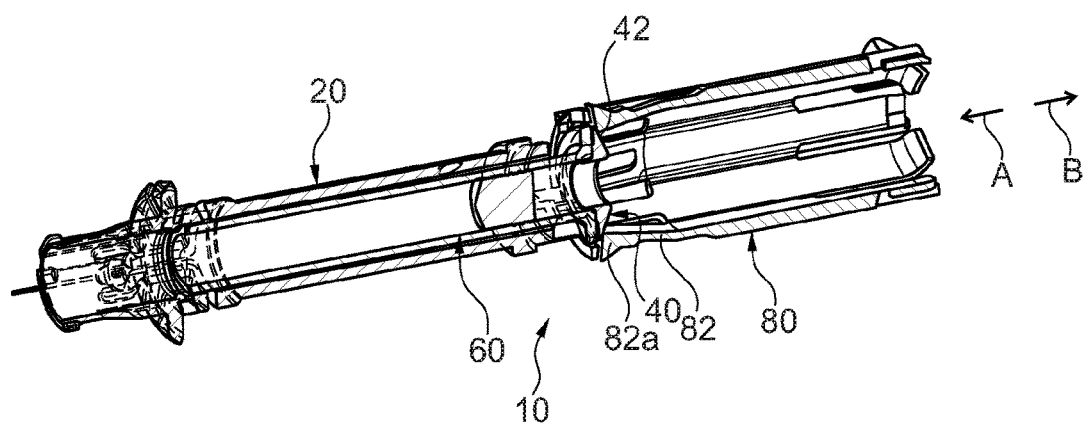
FIG. 4 shows a section view of an assembly according to an embodiment of the present invention with a syringe installed and a driving element engaging with the assembly.

FIG. 4 shows an example of an assembly 10 with a syringe 60 installed. Also shown is a drive element 80 having flexible legs 82 towards a forward end thereof. Each flexible leg 82 has a foot 82a at a forward end for engaging with the guard element 40. In the configuration shown in FIG. 4, the flexible legs 82 are flexed radially inwardly and are engaged with the guard element 40 so as to be capable of transmitting axial force thereto. Typically, the flexible legs 82 will be biased into their radially inward position due to interference with an outer sleeve or housing whose surface prevents radial outward flexing. Apertures or other suitable recesses or formations at predetermined axial locations on the outer sleeve or housing permit the flexible legs 82 to flex radially outwardly at a particular axial position. The conical or otherwise sloped surface 42 allow an adequate engagement between the drive element 80 and the guard element 40, but facilitate easy and reliable disengagement when the flexible legs 82 reach the predetermined axial location. The relationship and engagement/disengagement shown in and described in relation to FIG. 4 is not exclusive to the guard element described above using reference numeral 40. Indeed, the described relationship and engagement/disengagement may apply to any of guard elements 40',40" or any other guard element within the scope of the present invention.

Whilst it is preferable for the guard element of the present invention to act as a loading bridge that transmits axial force received from the rear of the guard element axially forwardly into the syringe support 20, the conical or otherwise sloped surface provides advantages that are independent of the preferable bridging feature. Therefore, according to some embodiments of the present invention, the guard element may have a conical or otherwise suitably sloped rearward facing surface but not have features that permit the guard element to behave as a loading bridge. Without the loading bridge features, axial forces received from axially rearward of the guard element will be transmitted directly through the guard element to the syringe on which the guard element is disposed and located. Thus, these embodiments will not mitigate the potential impact damage noted above to the same extent as the embodiments with the bridging features, however, it will provide a suitable rear surface for receiving the flexible legs of a driving element and facilitating easy and reliable disengagement. The risk of jamming is therefore reduced when used in an autoinjector device.

Figure 5:
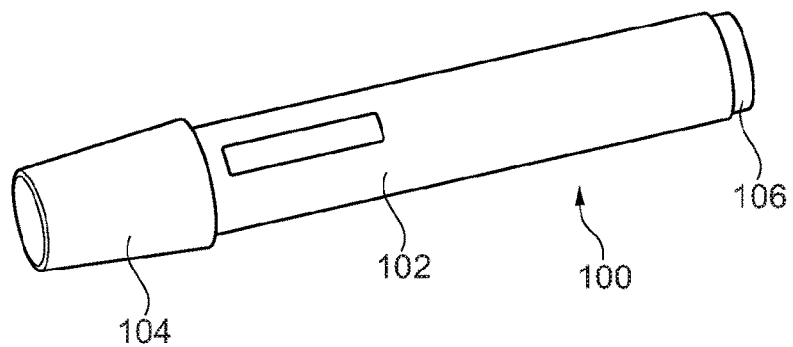
FIG. 5 shows an autoinjector device according to an embodiment of the present invention.

The assembly of the invention may form part of an autoinjector device. FIG. 5 shows an example of an autoinjector device 100 that may incorporate the assembly. The autoinjector device 100 shown in FIG. 5 includes a main body 102, a cap 104 removably attached to a front end of the main body 102, and a button 106 for actuating the autoinjector device 100.

The assembly and autoinjector of the invention is suitable for the injected delivery of drug, particularly for the treatment and/or prophylaxis of a number of diseases, disorders or conditions, including infections (viral, e.g. HIV infection, bacterial, fungal and parasitic); endotoxic shock associated with infection; inflammatory diseases/autoimmunity such as osteoarthritis, rheumatoid arthritis, psoriatic arthritis, systemic lupus erythematosus (SLE), ankylosing spondilitis, COPD, asthma, Alzheimer's Disease, Crohn's disease, ulcerative colitis, irritable bowel syndrome and psoriasis; immune mediated inflammatory disorders of the central and peripheral nervous system such as multiple sclerosis and Guillain-Barr syndrome; graft-versus-host disease; organ transplant rejection; pain; cancer (including solid tumours such as melanomas, hepatoblastomas, sarcomas, squamous cell carcinomas, transitional cell cancers, ovarian cancers and hematologic malignancies, acute myelogenous leukaemia, chronic myelogenous leukemia, gastric cancer and colon cancer); congenital disorders, e.g. cystic fibrosis and sickle cell anaemia; growth disorders; epilepsy; treatment of infertility; heart disease including ischaemic diseases such as myocardial infarction as well as atherosclerosis and intravascular coagulation; bone disorders such as osteopenia and osteoporosis; and metabolic/idiopathic disease, e.g. diabetes.

In embodiments, the syringe of the assembly and autoinjector herein contains a liquid drug formulation, which is designed for refrigerated rest (e.g. at from 2-8° C.) and for injected delivery at room temperature (e.g. at or about 18-30° C.). In embodiments, the viscosity of the liquid drug formulation is less than 120 mPa·s (120 centipoise), in embodiments less than 100 mPa·s (100 centipoise) at a delivery temperature of 20° C.

Appropriate drugs may thus be selected from biologically active agents, including chemical entities, polysaccharides, steroids and, especially, naturally occurring and recombinant proteins, including glycoproteins, polypeptides and oligopeptides and polymeric derivatives thereof. Particular proteins, polypeptides and oligopeptides include hormones, such as insulin, epinephrine, norepinephrine, adrenocorticotrophin, somatotropin, erythropoietin and oxytocin; cytokines, such as lymphokines, chemokines and interleukins and receptors therefor, e.g. interleukin (IL)-1α, IL-1β, IL-1R, IL-2, IL-3, IL-4, IL-5, IL-6, IL-13, IL17, interferon (IFN)-α, IFN-β, IFN-γ, granulocyte monocyte colony stimulating factor, tumour necrosis factor-a; growth factors, such as nerve growth factor and platelet-derived growth factor; enzymes, such as tissue plasminogen activator; and, especially, immunoglobulins. Immunoglobulins include whole antibodies and functionally active fragments and/or derivatives thereof, for example polyclonal, monoclonal, recombinant, multi-valent, mono- or multi-specific, humanised or chimeric antibodies, single chain antibodies, Fab fragments, Fab' and F(ab')2 fragments. Polymeric derivatives of such proteins, polypeptides and oligopeptides include derivatives formed between the protein, polypeptide or oligopeptide and a naturally occurring or synthetic polymer, e.g. a polysaccharide or a polyalyklene polymer such as a poly(ethyleneglycol) [PEG] or derivative thereof, e.g. methoxypoly (ethyleneglycol) [mPEG]. Particular agents include growth hormones and hormones for the treatment of infertility. Other particular agents are for the treatment of epilepsy such as brivaracetam and seletracetam.

The autoinjector device herein has been found to be of particular utility where the drug is an immunoglobulin or a fragment thereof, especially a PEGylated or mPEGylated antibody fragment.

The liquid drug formulations herein are typically aqueous formulations, which comprise the drug in solution and additionally other optional formulation components, which may include buffers (e.g. lactate, acetate), NaCl, and pH modifiers (e.g. NaOH).

The assembly and autoinjector device herein has been found to be of particular utility wherein the concentration of the drug (e.g. a therapeutic biologic type drug) in the liquid drug formulation is quite high. In particular, where the drug is a pegylated antibody the auto-injector device has been found to be of particular utility wherein the concentration of the drug is greater than 100 mg/ml, particularly greater than 150 mg/ml such as 200 mg/ml.

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

The invention claimed is:

1. An assembly for an autoinjector device, the assembly including:
   a syringe support for carrying a syringe installed therein, wherein the syringe support supports the syringe at a forward end of the syringe such as to limit forward axial movement of the syringe relative to the syringe support; and
   a guard element attachable to the syringe support;

wherein the guard element is attachable to the syringe support so that the guard element is axially restrained both axially forwardly and axially rearwardly relative to the syringe support, wherein attachment of the guard element to the syringe support includes abutment of first abutment features on the syringe support and second abutment features on the guard element;

wherein abutment of the first and second abutment features prevents forward axial movement of the guard element relative to the syringe support;

and wherein forwardly directed axial loads received by an axially rearward surface of the guard element are transmitted to the syringe support via the abutment of the first and second abutment features without applying axial loading to a syringe carried by the syringe support.

2. An assembly according to claim 1, wherein the guard element is attachable to a rear end of the syringe support.

3. An assembly according to claim 1, wherein the second abutment features of the guard element include a plurality of axially forwardly extending legs, and the first abutment features of said syringe support include an external flange, and forward axial movement of the guard element relative to the syringe support is limited by abutment of said plurality of axially forwardly extending legs against said external flange.

4. An assembly according to claim 3, wherein said plurality of axially forwardly extending legs form part of at least a pair of clasps, where each clasp includes a pair of the axially forwardly extending legs and a front cross beam extending circumferentially to connect the two legs of each pair of axially forwardly extending legs.

5. An assembly according to claim 4, wherein each of said front cross beams forms the axially forwardmost portion of each respective clasp.

6. An assembly according to claim 5, wherein an axially forwardly facing surface of each front cross beam is tapered, the axially forwardly facing surface extending axially rearwardly in a radially outward direction, and an axially rearwardly facing surface of said external flange is also tapered in at least parts of said external flange, the axially rearwardly facing surface of said external flange at said parts of said external flange extending axially rearwardly in a radially outward direction so as to be complementary to the axially forwardly facing surface of each front cross beam.

7. An assembly according to claim 4, wherein the syringe support includes third abutment features and the guard element includes fourth abutment features and rearward axial movement of the guard element relative to the syringe support is limited by the abutment of the third and fourth abutment features.

8. An assembly according to claim 7, wherein the third abutment features of the syringe support include outwardly radially extending elbows and the fourth abutment features of said guard element include said front cross beams and rearward axial movement of the guard element relative to the syringe support is limited by the abutment of the elbows against said front cross beams.

9. An assembly according to claim 8, wherein axially rearwardly extending legs extend from said elbows.

10. An assembly according to claim 9, wherein said front cross beams have a recessed portion for facilitating assembly of the front cross beams over the axially rearwardly extending legs of said syringe support.

11. An assembly according to claim 8, wherein said clasps each include a second cross beam that extends circumferentially to connect the two legs of each pair of axially forwardly extending legs, each second cross beam being axially rearward and axially spaced from the respective front cross beam.

12. An assembly according to claim 4, wherein the syringe support includes hooks that are configured to latch onto the guard element and limit rearward axial movement of the guard element relative to the syringe support.

13. An assembly according to claim 12, wherein each of said hooks is disposed on an axially rearwardly extending leg of the syringe support.

14. An assembly according to claim 1, wherein the axially rearward surface is an axially rearward surface of a flange.

15. An assembly according to claim 14, wherein said guard element defines a central bore extending in an axial direction and the flange extends radially outwardly from the bore.

16. An assembly according to claim 15, wherein the axially rearward facing surface of the flange slopes axially forwardly along radial directions away from said bore.

17. An assembly according to claim 15, wherein said guard element further comprises locating features for co-axially aligning the guard element with the rear end of a syringe.

18. An assembly according to claim 17, wherein said locating features comprise an axially forwardly extending spigot extending from an axially forwardly facing surface of the flange, the spigot defining part of said bore.

19. An assembly according to claim 18, wherein the guard element is assembled on the syringe support.

20. An assembly according to claim 19, further comprising a syringe supported by said syringe support, wherein at least part of said guard element is axially rearward of at least part of said syringe.

21. An assembly according to claim 20, wherein said syringe comprises a barrel having an outlet at a forward end, a needle fluidly connected to said outlet, an open rear end, a plunger element moveable within said barrel, a plunger rod connected to said plunger element for moving said plunger element within said barrel, and a rear syringe flange extending radially outwardly from a rear end of the barrel.

22. An assembly according to claim 21, wherein an axially forwardly facing side of the guard element is shaped so as to be complementary to the profile of the rear syringe flange.

23. An assembly according to claim 21, wherein the spigot is shaped so as to be complementary to the profile of the open rear end of the barrel.

24. An assembly according to any of claim 20, wherein the syringe contains a liquid drug formulation.

25. An assembly according to claim 24, wherein the barrel of said syringe has a volume corresponding to a single dose of said liquid drug formulation.

26. An assembly according to claim 24, wherein the liquid drug formulation comprises an aqueous formulation of a therapeutic biologic type drug.

27. An assembly according to claim 14, wherein said axially rearward facing surface of said flange corresponds to part of the surface of a conic frustum.

28. An assembly according to claim 1, wherein abutment of the first and second abutment features acts as an end-stop to prevent forward axial movement of the guard element relative to the syringe support.

29. An assembly according to claim 1, wherein the syringe support has a generally tubular body arranged for insertion therein of a syringe barrel of the syringe.

30. An assembly for an autoinjector device, the assembly including:
- a syringe support for supporting a syringe by limiting forward axial movement of the syringe relative to the syringe support; and
- a guard element attachable to the syringe support;
- wherein the guard element is attachable to the syringe support so that the guard element is axially restrained both axially forwardly and axially rearwardly relative to the syringe support,
- wherein attachment of the guard element to the syringe support includes abutment of first abutment features on the syringe support and second abutment features on the guard element;
- wherein forward axial movement of the guard element relative to the syringe support is limited by the abutment of the first and second abutment features;
- wherein forwardly directed axial loads received by an axially rearward surface of the guard element are transmitted to the syringe support via the abutment of the first and second abutment features;
- wherein the second abutment features of the guard element include a plurality of axially forwardly extending legs, and the first abutment features of said syringe support include an external flange, and forward axial movement of the guard element relative to the syringe support is limited by abutment of said plurality of axially forwardly extending legs against said external flange;
- wherein said plurality of axially forwardly extending legs form part of at least a pair of clasps, where each clasp includes a pair of the axially forwardly extending legs and a front cross beam extending circumferentially to connect the two legs of each pair of axially forwardly extending legs;
- wherein the syringe support includes hooks that are configured to latch onto the guard element and limit rearward axial movement of the guard element relative to the syringe support;
- wherein each of said hooks is disposed on an axially rearwardly extending leg of the syringe support; and
- wherein the legs of each of said pair of axially forwardly extending legs of each clasp are circumferentially spaced to receive one of said axially rearwardly extending legs of said syringe support.

31. An assembly according to claim 30, wherein said front cross beams have a recessed portion for facilitating assembly of the front cross beams over the axially rearwardly extending legs of said syringe support.

32. An autoinjector device including the assembly of claim 19.

33. An assembly for an autoinjector device, the assembly including:
- a syringe support for carrying a syringe installed therein, by limiting forward axial movement of the syringe relative to the syringe support; and
- a guard element attachable to the syringe support;
- wherein the guard element is attachable to the syringe support so that the guard element is axially restrained both axially forwardly and axially rearwardly relative to the syringe support,
- wherein attachment of the guard element to the syringe support includes abutment of first abutment features on the syringe support and second abutment features on the guard element;
- wherein abutment of the first and second abutment features prevents forward axial movement of the guard element relative to the syringe support;
- wherein forwardly directed axial loads received by an axially rearward surface of the guard element are transmitted to the syringe support via the abutment of the first and second abutment features without applying axial loading to a syringe carried by the syringe support;
- wherein the axially rearward surface is an axially rearward surface of a flange;
- wherein said guard element defines a central bore extending in an axial direction and the flange extends radially outwardly from the bore;
- wherein said guard element further comprises locating features for co-axially aligning the guard element with the rear end of a syringe; and
- wherein said locating features comprise an axially forwardly extending spigot extending from an axially forwardly facing surface of the flange, the spigot defining part of said bore.

* * * * *